(12) United States Patent
France

(10) Patent No.: US 6,440,918 B1
(45) Date of Patent: Aug. 27, 2002

(54) PARTICULATE COMPOSITIONS HAVING A PLASMA-INDUCED, GRAFT POLYMERIZED, WATER-SOLUBLE COATING AND PROCESS FOR MAKING SAME

(75) Inventor: Paul Amaat France, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/744,273
(22) PCT Filed: Jul. 23, 1999
(86) PCT No.: PCT/IB99/01314
§ 371 (c)(1),
(2), (4) Date: Jan. 22, 2001
(87) PCT Pub. No.: WO00/06687
PCT Pub. Date: Feb. 10, 2000

Related U.S. Application Data
(60) Provisional application No. 60/094,565, filed on Jul. 29, 1998.

(51) Int. Cl.$^7$ ............................. C11D 1/00; C11D 11/00; C11D 17/00
(52) U.S. Cl. ..................... 510/349; 510/224; 510/441; 510/445; 510/446; 523/106; 523/107
(58) Field of Search ................................. 510/349, 441, 510/445, 446, 224; 523/106, 107

(56) References Cited

U.S. PATENT DOCUMENTS

| | | | |
|---|---|---|---|
| 3,421,930 A | 1/1969 | Know et al. | ................ 117/93.1 |
| 4,756,844 A | 7/1988 | Walles et al. | .................. 252/95 |
| 4,810,524 A | 3/1989 | Nakayama et al. | ............ 427/38 |
| 5,595,762 A | 1/1997 | Derrieu et al. | .............. 424/490 |
| 6,340,664 B1 * | 1/2002 | Gassenmeier et al. | ...... 510/441 |

FOREIGN PATENT DOCUMENTS

| | | | |
|---|---|---|---|
| EP | 0 271 992 A2 | 6/1988 | ........... C11D/3/395 |
| EP | 0 716 144 A2 | 11/1995 | ........... C11D/17/00 |
| EP | 0 574 352 A1 | 6/1996 | ......... C08F/291/18 |
| GB | 1 269 018 | 3/1972 | ............. B05C/3/02 |
| GB | 2 252 559 A | 8/1992 | ............. C08F/2/52 |
| WO | WO 97/21497 | 6/1997 | ............ B05D/7/24 |

* cited by examiner

*Primary Examiner*—Gregory Delcotto
(74) *Attorney, Agent, or Firm*—Julia A. Glazer; Kim William Zerby; Steven W. Miller

(57) ABSTRACT

A composition having a plasma-induced, graft polymerized, water-soluble coating for controlling solubility, chemical stability and physical properties is disclosed. A process for making such a composition is also disclosed which involves subjecting a particulate material to plasma after which a water-soluble organic monomer is graft polymerized onto at least a portion of the particulate material. The compositions are particulate or non-particulate in form and can be used in shampoos, skin care and other cosmetic products, deodorant products, laundry, dishwashing, or other similar detergent products.

11 Claims, No Drawings

PARTICULATE COMPOSITIONS HAVING A PLASMA-INDUCED, GRAFT POLYMERIZED, WATER-SOLUBLE COATING AND PROCESS FOR MAKING SAME

This application claims priority from provisional application No. 60/094,565, filed Jul. 29, 1998.

FIELD OF THE INVENTION

The present invention generally relates to particulate compositions, and more particularly, to particulate compositions which have a plasma-induced, graft polymerized, water-soluble coating. The particulate compositions may be used in shampoos, skin care and other cosmetic products, deodorant products, laundry, dishwashing, carwashing and other similar applications. The plasma-induced, graft polymerized, water-soluble coating can control solubility, dispersion, flowability, enhance chemical stability or be a functional additive to the particulate composition. The invention also provides a process for making such plasma-induced, graft polymerized, coated particulate compositions.

BACKGROUND OF THE INVENTION

Currently, formulators of various cosmetic, laundry, dishwashing, shampoo, and other particulate-containing compositions are faced with numerous problems which impede delivering the active ingredients and attaining the full benefit of all of the ingredients in such compositions. By way of example, recent low dosage or "compact" detergent products experience dissolution problems, especially in cold temperature laundering solutions (i.e., less than about 30° C.). More specifically, poor dissolution results in the formation of "clumps" which appear as solid white masses remaining in the washing machine or on the laundered clothes after conventional washing cycles. These "clumps" are especially prevalent under cold temperature washing conditions and/or when the order of addition to the washing machine is laundry detergent first, clothes second and water last (commonly known as the "Reverse Order Of Addition" or "ROOA"). Similarly, this clumping phenomenon can contribute to the incomplete dispensing of detergent in washing machines equipped with dispenser drawers or in other dispensing devices, such as a granulette. In this case, the undesired result is undissolved detergent residue in the dispensing device.

Another similar problem with detergent compositions, especially granular laundry and dishwashing detergents, is the degradation of physical properties over extended storage periods. More particularly, spray dried granules and other particulate detergent ingredients have a tendency to "cake" while stored in the detergent box, especially under highly humid conditions. Such "caking" is very unacceptable to consumers and can lead to difficulties in "scooping" or otherwise removing the detergent from the box in which it is contained. This problem can also result in improper dosing of the laundering solution resulting in decreased cleaning performance. Other problems include chemical instability of the detergent composition and difficulty in dispersing polymers into wash solutions. Heretofore, detergent formulators have unsuccessfully attempted to resolve or minimize all of the aforementioned problems, and they continue to search for convenient solutions which do not affect other properties of the detergent composition.

Accordingly, despite the above disclosures in the art, there is a need for compositions, and a process for making such compositions, which have improved physical properties, solubility and/or chemical stability.

SUMMARY OF THE INVENTION

The invention meets the above-identified needs by providing a composition having a plasma-induced, graft polymerized, water-soluble coating for controlling solubility, chemical stability and physical properties. The invention also provides a process for making such a composition involving subjecting a particulate material to a plasma glow zone to form free radicals onto the surface, after which an organic hydrophilic monomer is introduced such that it ultimately deposits on the particular material by graft polymerization to form a water soluble coating. The plasma glow zone is contained in a plasma chamber and operated at selected power and pressures so as not to destroy or otherwise alter the functionality or stability of the coating or the particulate material that is being coated.

In accordance with one aspect of the invention, a composition is provided. The composition comprises a particulate material having at least a portion which has a plasma-induced, graft polymerized, water-soluble coating, wherein the water-soluble coating is formed by ionizing gas in a plasma chamber to form free radicals on the portion of the particulate material after which an organic hydrophilic monomer is deposited onto the portion of the particulate material by graft polymerization so as to form the water-soluble coating on the portion of the particulate material.

In accordance with yet another aspect of the invention, a process for producing a water-soluble composition is provided. The process comprises the steps of: (a) providing a particulate material; (b) subjecting at least a portion of the particulate material to plasma glow zone in which a gas is ionized to form free radicals on the portion of the particulate material, wherein the plasma glow zone is contained in a plasma chamber operated at a pressure of from about 1 mTorr to about 300 Torr and a power of from about 0.1 Watts to about 500 Watts; (c) introducing a water-soluble, organic hydrophilic monomer into the chamber after the step (b) such that the organic hydrophilic monomer reacts with the free radicals on the portion of the particulate material so as to form a water-soluble coating on the portion of the particulate material.

As used herein, the "plasma glow zone" is the space or region where plasma is generated using electricity, such as the space between two electrodes in a plasma vacuum chamber. As used herein, the phrase "plasma chamber" or "plasma vacuum chamber" includes or can be embodied in fluidized beds, tumbling drums, vibrating belts and other similar apparatus. All percentages, ratios and proportions used herein are by weight, unless otherwise indicated. All documents including patents and publications cited herein are incorporated herein by reference.

Accordingly, it is an advantage of the invention to provide a composition which has improved physical properties, solubility and/or chemical stability. It is also an advantage of the invention to provide a process for producing such compositions in an convenient manner. These and other advantages and features of the present invention will become apparent to those skilled in the art from a reading of the following detailed description of the preferred embodiments and the appended claims.

DETAILED DESCRIPTION OF THE PREFERRED EMBODIMENT

In essence, the invention is directed to particulate and non-particulate compositions having a plasma-induced, graft polymerized, water-soluble coating. In preferred modes of the invention, the particulate material is selected from water-insoluble particles such as those used in cosmetic and shampoo compositions, soluble particles such as spray dried granules, agglomerates and mixtures thereof which are typically used in detergent compositions. The non-particulate compositions herein may also be used in laundry or dishwashing, for example, as a laundry or dishwashing tablet, block, cylinder, sheet, cube or other non-particulate configuration. The graft polymerization of the water-soluble coating by exposing the particulate or non-particulate material to an organic hydrophilic monomer after the particulate or non-particulate material is subjected to plasma. It is essential for the graft polymerization process step that the organic monomer be introduced after the plasma has been generated in the plasma chamber.

Preferably, the water-soluble coating is formed from an organic hydrophilic monomer, which is even more preferably selected from the group consisting of acrylates, methacrylates, acrylamides, methacrylamides, maleates, filmarates, vinyl ethers and mixtures thereof More preferably, the organic monomer is selected from the group consisting of 2-hydroxyethyl methacrylate, N,N-dimethylacrylamide, acrylic acid, methacrylic acid and mixtures thereof. Most preferably, the organic monomer is acrylic acid.

The water-soluble coating is on at least a portion of the compositions described herein. By "at least a portion", it is meant that at least 1%, preferably 90% to 100% of the particulate or non-particulate composition has a water-soluble coating on it. It should be understood that not all of the composition needs to be coated to be within the scope of the invention. To that end, a plasma coating process is used to place the water-soluble coating on the composition. As detailed hereinafter, this is accomplished by ionizing a gas, such as argon, using high frequency electricity in a plasma vacuum chamber. Suitable gases may be selected from the group consisting of argon, helium, oxygen, nitrogen and mixtures thereof. As used herein, the phrase "plasma-induced, graft polymerized" means that which has been deposited, coated or otherwise layered using one or more of grafting deposition techniques wherein the material to be deposited reacts, grafts, attaches, bonds or otherwise binds with the free radicals formed on the surface of the material during generation of plasma in a plasma chamber.

Typical plasma chambers will have a "plasma glow zone" which can be the region between the two electrodes used to generate the high frequency electricity, and thus the plasma therebetween. The pressure inside the plasma chamber is typically maintained at a pressure of from about 5 mTorr to about 300 Torr, more preferably from about 10 mTorr to about 1 Torr, and most preferably from about 50 mTorr to about 250 mTorr. The power used in the plasma chamber is selected to be from about 0.1 Watts to about 500 Watts, more preferably from about 0.5 Watts to about 100 Watts, and most preferably from about 1 Watt to about 10 Watts.

This application of a high frequency electric field to a gas to form a plasma of gas ions is a known technique used in polymerization of monomers such as organic hydrophilic monomers which are suitable for use herein to form the water-soluble coating on the detergent composition. This technique has been described, for example, in Luster, U.S. Pat. No. 2,257,177. In general, this involves continuous contact of the polymerizing monomer in the vapor phase with the gas plasma until substantial completion of the graft polymerization on the substrate. This technique tends to form a cross-inked product as suggested by U.S. Pat. No. 3,287,242. Due to the high cross-linking associated with plasma polymerization, that technique is generally employed for the purpose of forming water-insoluble thin films or coatings rather than the water-soluble coating currently contemplated by the present invention. The activation is confined to a region near the surface of the substrate at which links and cross-links are formed.

One modification of the film/coating forming techniques in which the monomer is polymerized directly from the gas state is described in Knox et al, U.S. Pat. No. 3,475,307. There, the substrate is cooled to condense a thin layer of liquid monomer on the substrate in order to increase the polymerization rate. However, in that technique, the ordinary skilled artisan must avoid condensing "too much" of the monomer on the surface because otherwise the incoming activated molecules from the gas phase would not reach the monomer removed from the gas liquid interface which is stated to cause a coating of little adherence (col. 10, lines 54–60). The order of magnitude of condensed monomer prior to polymerization is indicated as being few molecules in thickness (col. 4, lines 1–4).

Another plasma coating technique is to initiate polymerization by use of a non-equilibrium ionized gas plasma and to complete the majority of the polymerization in the absence of the plasma. In this manner, a high molecular weight polymer is formed. The formation of the ionized gas plasma may be accomplished in any of the techniques known to produce such plasmas. For example, see J. R. Hollahan and A. T. Bell, eds., "Techniques in Applications of Plasma Chemistry", Wyley, New York, 1974 and M Shen, ed. "Plasma Chemistry of Polymers", Dekker, New York, 1976. In one technique, an ionizable gas is contained under vacuum between parallel plate electrodes connected to a radio frequency generator which is sold by International Plasma Corporation under the designation "Model 3001". The plasma can be created with such parallel plates either external or internal to the plasma chamber. In another technique, an external induction coil creates an electric field which produces the plasma of ionized gas. In yet another technique, oppositely charged electrode points are placed directly into the plasma vacuum chamber in spaced apart relationship to create the plasma. Any plasma formed by these techniques or any other one in which an electric field creates a path of electrical conduction totally within the gas phase is suitable for use in the invention.

As used herein, the term "plasma" is to be distinguished from any liquid or solid environment in which an electric field is applied to create ions in a path through the solid or liquid. This is not to exclude the possibility that an electric field would also be applied across the non-vapor monomer. However, if it were, it is not believed that it would have any beneficial function; instead, it would be extraneous to the vapor phase plasma. The operating parameters for the plasma vary from monomer to monomer. In general, it is preferable to employ reduced gas pressures to form a glow discharge by electron liberation which causes ionization in the gas phase. Where a plasma is created in a chamber including a gas at a pressure below atmospheric pressure, the plasma is formed when the interelectrode potential exceeds a threshold value which is sufficient to ionize or "break-down" the gas. This is a function of the composition of the gas, its pressure and the distance between the electrodes. After breakdown, the gas is conductive and a stable plasma may be maintained over a wide range of currents. Although the exact composition of the plasma is not known, it is believed to include electrons, ions, free radicals, and other reactive species.

In a related procedure, the creation of active sites on the substrate or particulate material may be facilitated by direct activation from the ionized gas. For this purpose, the presence of any ionizable gas under the conditions prevalent in the plasma may be employed. For example, water vapor may be ionized to create active polymerization sites for certain monomers. Other gases which have been ionized by such plasmas include hydrogen chloride, carbon tetrachloride, and inert gases such as helium or neon. Those gases which are ionizable in the plasma are well known to those in the field. The monomer to be deposited may be in the essentially pure monomeric state or in solution. In the latter instance, organic or inorganic solvents capable of complete dissolution of the monomer may be employed. Typical organic solvents for certain monomers include benzene and acetone.

For any given plasma deposition technique as described herein, the process may involve the use of high frequency microwaves to ionize the gas in the plasma chamber. Alternatively, high frequency radio waves or direct current electricity can be used, for example to ionize the gas between two oppositely charged electrode points used to define the plasma glow zone in a plasma vacuum chamber. Another option is to pulsate or otherwise intermittently ionize the gas in the plasma glow zone in the plasma chamber so as to control the plasma-induced deposition of the monomer onto the particulate detergent material. Further control of plasma-induced deposition can be achieved in the process of the present invention by positioning the particulate detergent material to be coated with the hydrophilic monomer outside of the plasma glow zone. Alternatively or additionally, the water-soluble hydrophilic monomer may be introduced outside of the plasma glow zone, as well, to provide further control of the deposition.

The particulate or non-particulate material subsequent to being subjected to plasma is subsequently (i.e., after the plasma has been generated in the plasma chamber) exposed to an organic hydrophilic monomer that is ultimately graft polymerized onto at least a portion of the particulate or non-particulate surface. So-called "graft polymerization" is known and has been used in the art with many graft copolymers such as ABS (acrylonitrile butadiene/styrene) resins which have achieved considerable commercial success. It has also been known in the art that various vinyl monomers can be graft polymerized onto polymer substrates which have been first treated with ionizing radiation in the presence of oxygen or with ozone to form peroxy groups on the surface of said substrate. U.S. Pat. No. 3,008,920 and U.S. Pat. No. 3,070,573 teach the grafting of selected monomers onto ozonated surfaces. However, problems have also arisen when such a graft polymerization is carried out. For example, one serious complication involves graft polymerization of the vinyl monomer onto the substrate as desired, but with the simultaneous and undesired homopolymerization or crosslinking of the vinyl monomer which leads to a water-insoluble coating. By contrast, the present invention relates to a composition and process for modifying the surface characteristics of a particulate substrate with minimum of crosslinking to obtain a water-soluble coating. In that regard, operating the plasma chamber at the selected power and pressure levels described previously is important. Typically, the graft polymerization of the organic monomer will take from about 1 minute to about 40 minutes, preferably 10 minutes to about 30 minutes.

The organic monomer may be in the form of a liquid, a solid, or a solid-liquid mixture. For the liquid monomer, the monomer vapor is supplied by evaporation of monomer into the plasma which is facilitated by the application of a vacuum. Similarly, for the solid monomer, such free radicals and/or ions are supplied by sublimed monomer vapor. For simplicity of description, the non-vapor monomer to be activated will be described herein as being in the liquid state unless otherwise specified.

Water-Soluble Coating

As mentioned previously, the water-soluble coating is formed from an organic hydrophilic monomer, some of which are mentioned above. The compositions preferably contain an effective amount of such monomer so as to achieve the desired solubility, flowability, chemical stability and/or other desired function for the particulate or non-particulate composition. In typical formulations, the coating which is formed of the monomer grafted onto the particulate or non-particulate composition will have a thickness in the range of from about 0.01 microns to about 1000 microns, more preferably from about 0.05 microns to about 50 microns and most preferably from about 0.1 microns to about 10 microns.

Suitable organic hydrophilic monomers include generally water soluble conventional vinyl monomers such as: acrylates and methacrylates of the general structure

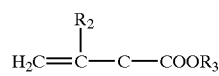

where $R_2$ is hydrogen or methyl and $R_3$ is hydrogen or is an aliphatic hydrocarbon group of up to about 10 carbon atoms substituted by one or more water solublizing groups such as carboxy, hydroxy, amino, lower alkylamino, lower dialkylamino, a polyethylene oxide group with from 2 to about 100 repeating units, or substituted by one or more sulfate, phosphate, sulfonate, phosphonate, carboxamido, sulfonanido or phosphonamido groups, or mixtures thereof;

acrylamides and methyacrylamides of the formula

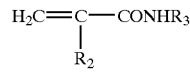

where $R_2$ and $R_3$ are as defined above;

acrylamides and methyacrylamides of the formula

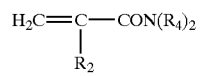

where $R_4$ is lower alkyl of 1 to 3 carbon atoms and $R_2$ is as defined above;

maleates and funmarates of the formula

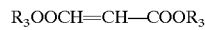

wherein $R_3$ is as defined above;

vinyl ethers of the formula

where $R_3$ is as defined above;

aliphatic vinyl compounds of the formula

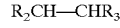

where $R_2$ is as defined above and $R_3$ is as defined above with the proviso that $R_3$ is other than hydrogen; and vinyl substituted heterocycles, such as vinyl pyridines, peperidines and imidazoles and N-vinyl lactams, such as N-vinyl-2-pyrrolidone.

Included among the useful water-soluble monomers are: 2-hydroxyethyl-, 2- and 3-hydroxypropyl-, 2,3-dihydroxypropyl-, polyethoxyethyl-, and polyethoxypropyl acrylates, methacrylates, acrylamides and methacrylamides; acrylamide, methacrylamide, N-methylacrylamide, N-methylmethacrylamide, N, N-dimethylacrylamide, N, N-dimethylmethacrylamide; N, N-dimethyl- and N, N-diethyl-aminoethyl acrylate and methacrylate and the corresponding acrylarides and methacrylamides; 2- and 4-vinylpyridine; 4- and 2-methyl-5-vinylpyridine; N-methyl4-vinylpiperidine; 2-methyl-1-vinylimidazole; N, N-dimethylallyamine; dimethylaminoethyl vinyl ether, N-vinylpyrrolidone; acrylic and methacrylic acid; itaconic, crotonic, fumaric and maleic acids and the lower hydroxyalkyl mono and diesters thereof, such as the 2-hydroxyethyl fumarate and maleate, sodium acrylate and methacrylate; maleic anhydride; 2-methacryloyloxyethylsulfonic acid and allylsulfonic acid.

Preferred water soluble monomers include 2-hydroxyethylmethacrylate; N, N-dimethylacrylamide; acrylic acid and methacrylic acid; and most preferably 2-hydroxyethyl methacrylate.

DETERGENT COMPONENTS

The particulate and non-particulate compositions described herein can be in the form of detergent compositions which preferably contain a detersive surfactant and a detergent builder, and optionally, a variety of common detergent ingredients. The surfactant system of the detergent composition may include anionic, nonionic, zwitterionic, ampholytic and cationic classes and compatible mixtures thereof. Detergent surfactants are described in U.S. Pat. No. 3,664,961, Norris, issued May 23, 1972, and in U.S. Pat. No. 3,919,678, Laughlin et al., issued Dec. 30, 1975, both of which are incorporated herein by reference. Cationic surfactants include those described in U.S. Pat. No. 4,222,905, Cockrell, issued Sep. 16, 1980, and in U.S. Pat. No. 4,239,659, Murphy, issued Dec. 16, 1980, both of which are also incorporated herein by reference.

Nonlimiting examples of surfactant systems include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^-M^+)$ $CH_3$ and $CH_3$ $(CH_2)_y$ $(CHOSO_3^-M^+)$ $CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("$AE_xS$"; especially EO 1–7 ethoxy sulfates), $C_{10}$–$C_{18}$ alkyl alkoxy carboxylates (especially the EO 1–5 ethoxycarboxylates), the $C_{10-18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like, can also be included in the surfactant system. The $C_{10}$–$C_{18}$ N-alkyl polyhydroxy fatty acid amides can also be used. Typical examples include the $C_{12}$–C18 N-methylglucaiides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10-20}$ conventional soaps may also be used. If high sudsing is desired, the branched-chain $C_{10}$–$C_{16}$ soaps may be used. Mixtures of anionic and nonionic surfactants are especially useful. Other conventional useful surfactants are listed in standard texts.

The detergent composition can, and preferably does, include a detergent builder. Builders are generally selected from the various water-soluble, alkali metal, ammonium or substituted ammonium phosphates, polyphosphates, phosphonates, polyphosphonates, carbonates, silicates, borates, polyhydroxy sulfonates, polyacetates, carboxylates, and polycarboxylates. Preferred are the alkali metal, especially sodium, salts of the above. Preferred for use herein are the phosphates, carbonates, silicates, $C_{10-18}$ fatty acids, polycarboxylates, and mixtures thereof. More preferred are sodium tripolyphosphate, tetrasodium pyrophosphate, citrate, tartrate mono- and di-succinates, sodium silicate, and mixtures thereof (see below).

Specific examples of inorganic phosphate builders are sodium and potassium tripolyphosphate, pyrophosphate, polymeric metaphosphate having a degree of polymerization of from about 6 to 21, and orthophosphates. Examples of polyphosphonate builders are the sodium and potassium salts of ethylene diphosphonic acid, the sodium and potassium salts of ethane 1-hydroxy-1, 1-diphosphonic acid and the sodium and potassium salts of ethane, 1,1,2-triphosphonic acid. Other phosphorus builder compounds are disclosed in U.S. Pat. Nos. 3,159,581; 3,213,030; 3,422,021; 3,422,137; 3,400,176 and U.S. Pat. No. 3,400,148, all of which are incorporated herein by reference.

Examples of nonphosphorus, inorganic builders are sodium and potassium carbonate, bicarbonate, sesquicarbonate, tetraborate decahydrate, and silicates having a weight ratio of $SiO_2$ to alkali metal oxide of from about 0.5 to about 4.0, preferably from about 1.0 to about 2.4. Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, anmmonium and substituted ammonium salts of ethylene diarnine tetraacetic acid, nitrilotriacetic acid, oxydisuccinic acid, mellitic acid, benzene polycarboxylic acids, and citric acid.

Polymeric polycarboxylate builders are set forth in U.S. Pat. No. 3,308,067, Diehl, issued Mar. 7, 1967, the disclosure of which is incorporated herein by reference. Such materials include the water-soluble salts of homo- and copolymers of aliphatic carboxylic acids such as maleic acid, itaconic acid, mesaconic acid, fumaric acid, aconitic acid, citraconic acid and methylenemalonic acid. Some of these materials are useful as the water-soluble anionic polymer as hereinafter described, but only if in intimate admixture with the nonsoap anionic surfactant.

Other suitable polycarboxylates for use herein are the polyacetal carboxylates described in U.S. Pat. No. 4,144,226, issued Mar. 13, 1979 to Crutchfield et al., and U.S. Pat. No. 4,246,495, issued Mar. 27, 1979 to Crutchfield et al., both of which are incorporated herein by reference. These polyacetal carboxylates can be prepared by bringing together under polymerization conditions an ester of glyoxylic acid and a polymerization initiator. The resulting polyacetal carboxylate ester is then attached to chemically stable end groups to stabilize the polyacetal carboxylate against rapid depolymerization in alkaline solution, converted to the corresponding salt, and added to a detergent composition. Particularly preferred polycarboxylate builders are the ether carboxylate builder compositions comprising a combination of tartrate monosuccinate and tartrate disuccinate described in U.S. Pat. No. 4,663,071, Bush et al., issued May 5, 1987, the disclosure of which is incorporated herein by reference.

Water-soluble silicate solids represented by the formula $SiO_2 \cdot M_2O$, M being an alkali metal, and having a $SiO_2:M_2O$ weight ratio of from about 0.5 to about 4.0, are useful salts in the detergent granules of the invention at levels of from about 2% to about 15% on an anhydrous weight basis, preferably from about 3% to about 8%. Anhydrous or hydrated particulate silicate can be utilized, as well.

Any number of additional ingredients can also be included as components in the granular detergent composition. These include other detergency builders, bleaches, bleach activators, suds boosters or suds suppressors, anti-tarnish and anti-corrosion agents, soil suspending agents, soil release agents, germicides, pH adjusting agents, nonbuilder alkalinity sources, chelating agents, smectite clays, enzymes, enzyme-stabilizing agents and perfumes. See U.S. Pat. No. 3,936,537, issued Feb. 3, 1976 to Baskerville, Jr. et al., incorporated herein by reference.

Bleaching agents and activators are described in U.S. Pat. No. 4,412,934, Chung et al., issued Nov. 1, 1983, and in U.S. Pat. No. 4,483,781, Hartrnan, issued Nov. 20, 1984, both of which are incorporated herein by reference. Chelating agents are also described in U.S. Pat. No. 4,663,071, Bush et al., from Column 17, line 54 through Column 18, line 68, incorporated herein by reference. Suds modifiers are also optional ingredients and are described in U.S. Pat. No. 3,933,672, issued Jan. 20, 1976 to Bartoletta et al., and U.S. Pat. No. 4,136,045, issued Jan. 23, 1979 to Gault et al., both incorporated herein by reference.

Suitable smectite clays for use herein are described in U.S. Pat. No. 4,762,645, Tucker et al., issued Aug. 9, 1988, Column 6, line 3 through Column 7, line 24, incorporated herein by reference. Suitable additional detergency builders for use herein are enumerated in the Baskerville patent, Column 13, line 54 through Column 16, line 16, and in U.S. Pat. No. 4,663,071, Bush et al., issued May 5, 1987, both incorporated herein by reference.

COSMETIC COMPONENTS

The compositions of the present invention can also be in the form of cosmetic compositions or components thereof. Typically, such compositions contain insoluble particles at levels of from about 0.1% to about 20%, more preferably from about 0.25% to about 15%, and most preferably from about 0.5% to about 10%, based on the weight of the total composition. Such insoluble particles are useful for enhancing the cleansing effect, when the compositions of the present invention are in the form of a cleansing composition. The term "insoluble", as used herein, means that the particles are essentially insoluble in the compositions of the present invention. In particular, the insoluble particles should have a solubility less than about 1 gram per 100 grams of composition at 25.degree. C., preferably less than about 0.5 grams per 100 grams of composition at 25.degree. C., and more preferably less than about 0.1 grams per 100 grams of composition at 25.degree. C.

Useful herein are both micronized and conventional size insoluble particles. The micronized particles, for the most part, are of a size that is below the tactile threshold and are essentially nonabrasive to the skin. The conventional size particles are tactilely perceptible and are added for the scrubbing and abrasive effect which they provide.

The micronized particles have a mean particle size diameter and particle size distribution such that they are below the tactile perception threshold of most users, and yet are not so small as to be ineffective for aiding in oil, dirt, and debris (e.g., make-up) removal. It is found herein that particles having a mean particle size diameter greater than about 75 microns are tactilely perceived during the cleansing process mid it is important to minimize the amount of these larger particles if it is desired that the particles not be felt by the user. Conversely, it is found that particles having a mean particle size diameter of less than about 1 to about 5 microns are generally less effective for providing a cleansing benefit. Without being limited by theory, it is believed that the micronized cleansing particles should be of a size that is on the order of the thickness of the dirt, oil, or debris layer to be cleaned away. This layer is believed to be on the order of a few microns in thickness in most instances. It is therefore found in the present invention that the micronized particles should have a mean particle size diameter from about 1 to about 75 microns, more preferably from about 15 to about 60 microns, and most preferably from about 20 to about 50 microns, so as to provide effective cleansing without being tactilely perceptible. Particles having a wide range of shapes, surface characteristics, and hardness characteristics can be utilized herein provided the particle size requirements are met. Micronized particles of the present invention can be derived from a wide variety of materials including those derived from inorganic, organic, natural, and synthetic sources. Nonlimiting examples of these materials include those selected from the group consisting of almond meal, alumina, aluminum oxide, aluminum silicate, apricot seed powder, attapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, teflon (i.e. polytetrafluoroethylene), polyhalogenated olefins, pumice rice bran, rye flour, sericite, silica, silk, sodium bicarbonate, sodium silicoaluminate, soy flour synthetic hectorite, talc, tin oxide, titanium dioxide, tricalcium phosphate, walnut shell powder, wheat bran, wheat flour, wheat starch, zirconium silicate, and mixtures thereof. Also useful are micronized particles made from mixed polymers (e.g., copolymers, terpolymers, etc.), such as polyethylene/polypropylene copolymer, polyethylene/propylene/isobutylene copolymer, polyethylene/styrene copolymer, and the like. Typically, the polymeric and mixed polymeric particles are treated via an oxidation process to destroy impurities and the like. The polymeric and mixed polymeric particles can also optionally be crosslinked with a variety of common crosslinking agents, nonlimiting examples of which include butadiene, divinyl benzene, methylenebisacrylamide, allyl ethers of sucrose, allyl ethers of pentaerythritol, and mixtures thereof. Other examples of useful micronized particles include waxes and resins such as paraffins, camnuba wax, ozekerite wax, candellila wax, urea-formaldehyde resins, and the like. When such waxes and resins are used herein it is important that these materials are solids at ambient and skin temperatures.

Among the preferred water-insoluble, micronized particulate materials useful herein are the synthetic polymeric particles selected from the group consisting of polybutylene, polyethylene, polyisobutylene, polymethylstyrene, polypropylene, polystyrene, polyurethane, nylon, teflon, and mixtures thereof. Most preferred are polyethylene and polypropylene micronized particles, with the oxidized versions of these materials being especially preferred. Examples of commercially available particles useful herein include the ACumist.TM. micronized polyethylene waxes available from Allied Signal (Morristown, N.J.) available as the A, B, C, and D series in a variety of average particle sizes ranging from 5 microns to 60 microns. Preferred are the ACumist.™. A-25, A-30, and A45 oxidized polyethylene particles having a means particle size of 25, 30, and 45 microns, respectively. Examples of commercially available polypropylene particles include the Propyltex series available from Micro Powders (Dartek).

The conventional size insoluble particles are well-known to formulation chemists in the art. These particles typically have larger particle sizes than the micronized particles described herein. These particles generally have an average particle size diameter that is about 75 microns or greater, which is about the tactile threshold described above. These conventional size particles typically have average particle sizes ranging up to about 400 microns and larger. These particles can be made from the same materials as for the micronized particles just described. Among the preferred conventional size particulate materials useful herein are the synthetic polymeric particles selected from the group consisting of polybutylene, polyethylene, polyisobutylene, polymethyistyrene, polypropylene, polystyrene, polyurethane, nylon, teflon, and mixtures thereof. Most preferred are polyethylene and polypropylene micronized particles, with the oxidized versions of these materials being especially preferred. An example of a commercially available conventional size particle useful herein is ACuscrub.™. 51, available from Allied Signal (Morristown, N.J.) having a mean particle size of about 125 microns.

Other product forms containing plasma-coated particles in accordance with the invention are also contemplated. By way of example, McAtee et al, U.S. Pat. No. 5,665,364, and LaFleur et al, U.S. Pat. No. 5,683,706, disclose a cosmetic compositions and a variety of particulate ingredients suitable for plasma coating with a water-soluble coating according to the invention.

The following examples are presented for illustrative purposes only and are not to be construed as limiting the scope of the appended claims in any way.

EXAMPLE I

A dishwashing tablet having the formula set forth in Table I below is placed on the bottom electrode of a vacuum chamber of plasma discharge unit (commercially available from APS Inc., Model D). The plasma chamber is depressurized to 20 mTorr. A carrier gas mixture (Argon/Oxygen at 1/1 ratio) is continuously introduced into the chamber at a constant rate (10 sccm), so the pressure inside the chamber is maintained at 63 mTorr by the balance of continuous evacuation and introduction of the carrier gas. While maintaining the above-noted conditions, low temperature plasma is generated inside the chamber for a period of 5 minute by supplying high frequency electricity (200 Watts) at a frequency of 40 kHz so as to expose the surface of the tablet to the low temperature plasma. Thereafter, an organic hydrophilic monomer (acrylic acid) is introduced into the chamber at a constant rate to maintain constant pressure in the chamber at 200 mTorr for 10 minutes during which no plasma is generated and deposited onto the tablet. The chamber is evacuated (30 mTorr) and flooded with atmospheric air. The resultant tablet has a water-soluble coating formed of the deposited monomer. The water solubility of the tablet is unexpectedly equal to uncoated tablets and superior to tablets coated by means other than plasma deposition.

TABLE I

| Component | (% weight) I |
|---|---|
| Sodium tripolyphosphate | 38.3 |
| Sodium carbonate | 15.4 |
| Disilicate, Na (2.0 r) | 12.6 |
| Alkyl ethoxylate propoxylate | 2.2 |
| Sodium perborate | 12.2 |
| Amylase enzyme | 0.9 |
| Protease enzyme | 1.0 |
| Sodium Sulfate | 15.8 |
| Misc. (Perfume, water) | balance |
|  | 100.0 |

EXAMPLES II–IV

Several detergent compositions made in accordance with the invention and specifically for top-loading washing machines are coated with an acrylic monomer. Specifically, a prototype apparatus is configured using a modified, rotational vaporator with a 12 inch (30.5 cm) quartz tube for the treatment chamber and an external coil electrode wrapped over a 6 inch (15.25 cm) length. A 50 gram sample of detergent composition is placed in the plasma glow zone, and Argon gas is introduced into the plasma chamber which is maintained at 200 mTorr for 15 minutes min. at the output of 100 Watts by the inductive coupling system using a radio frequency power system of 13.6 mHz while rotating the cylinder of the reactor at 10 rpm. The detergent compositions are then plasma treated with oxygen for 15 minutes at the output of 100 Watts by the inductive coupling system using a radio frequency power system of 13.6 mHz while rotating the cylinder of the reactor at 10 rpm. After the plasma treatment, acrylic acid vapor is introduced into the chamber which is maintained at 500 mTorr and graft polymerization on the detergent compositions occurs for 20 minutes. The resulting compositions are exemplified below. The base granule is prepared by a conventional spray drying process in which the starting ingredients are formed into a slurry and passed though a spray drying tower having a countercurrent stream of hot air (200–300° C.) resulting in the formation of porous granules. The admixed agglomerates are formed from two feed streams of various starting detergent ingredients which are continuously fed, at a rate of 1400 kg/hr, into a Lödige CB-30 mixer/densifier, one of which comprises a surfactant paste containing surfactant and water and the other stream containing starting dry detergent material containing aluminosilicate and sodium carbonate. The rotational speed of the shaft in the Lödige CB-30 mixer/densifier is about 1400 rpm. The contents from the Lödige CB-30 mixer/densifier are continuously fed into a Lödige KM-600 mixer/densifier for further agglomeration. The resulting detergent agglomerates are then fed to a fluid bed dryer and to a fluid bed cooler before being admixed with the spray dried granules. The remaining adjunct detergent ingredients are sprayed on or dry added to the blend of agglomerates and granules.

|  | II | III | IV |
|---|---|---|---|
| Base Granule |  |  |  |
| Aluminosilicate | 18.0 | 18.0 | 22.0 |
| Sodium sulfate | 10.0 | 10.0 | 19.0 |
| Sodium polyacrylate polymer | 3.0 | 3.0 | 2.0 |
| Polyethylene Glycol (MW = 4000) | 2.0 | 2.0 | 1.0 |
| $C_{12-13}$ linear alkylbenzene sulfonate, Na | 6.0 | 6.0 | 7.0 |
| $C_{14-16}$ secondary alkyl sulfate, Na | 3.0 | 3.0 | 3.0 |
| $C_{14-15}$ alkyl ethoxylated sulfate, Na | 3.0 | 3.0 | 9.0 |
| Sodium silicate | 1.0 | 1.0 | 2.0 |
| Brightener 24[6] | 0.3 | 0.3 | 0.3 |
| Sodium carbonate | 7.0 | 7.0 | 25.7 |
| DTPA[1] | 0.5 | 0.5 | — |
| Admixed Agglomerates |  |  |  |
| $C_{14-15}$ alkyl sulfate, Na | 5.0 | 5.0 | — |
| $C_{12-13}$ linear alkylbenzene sulfonate, Na | 2.0 | 2.0 | — |
| Sodium Carbonate | 4.0 | 4.0 | — |
| Polyethylene Glycol (MW = 4000) | 1.0 | 1.0 | — |
| Admix |  |  |  |
| $C_{12-15}$ alkyl ethoxylate (EO = 7) | 2.0 | 2.0 | 0.5 |
| Perfume | 0.3 | 0.3 | 1.0 |
| Polyvinylpyrrilidone | 0.5 | 0.5 | — |
| Polyvinylpyridine N-oxide | 0.5 | 0.5 | — |
| Polyvinylpyrrolidone-polyvinylimidazole | 0.5 | 0.5 | — |
| Distearylamine & Cumene sulfonic acid | 2.0 | 2.0 | — |
| Soil Release Polymer[2] | 0.5 | 0.5 | — |
| Lipolase Lipase (100.000 LU/I)[4] | 0.5 | 0.5 | — |
| Termamyl amylase (60 KNU/g)[4] | 0.3 | 0.3 | — |
| CAREZYME ® cellulase (1000 CEVU/g)[4] | 0.3 | 0.3 | — |
| Protease (40 mg/g)[5] | 0.5 | 0.5 | 0.5 |
| NOBS[3] | 5.0 | 5.0 | — |
| Sodium Percarbonate | 12.0 | 12.0 | — |
| Polydimethylsiloxane | 0.3 | 0.3 | — |
| Miscellaneous (water, etc.) | balance | balance | balance |
| Total | 100 | 100 | 100 |

[1]Diethylene Triamine Pentaacetic Acid
[2]Made according to U.S. Pat. No. 5,415,807, issued May 16, 1995 to Gosselink et al
[3]Nonanoyloxybenzenesulfonate
[4]Purchased from Novo Nordisk A/S
[5]Purchased from Genencor
[6]Purchased from Ciba-Geigy The resulting detergent compositions unexpectedly have improved chemical stability and flowability.

EXAMPLES V–XVI

The following detergent compositions accordance with the invention are especially suitable for front loading washing machines and are coated with an acrylic acid monomer as described in Example II. The compositions are made in the manner of Examples II–IV.

| | (% Weight) | | |
|---|---|---|---|
|  | V | VI | VII |
| Base Granule |  |  |  |
| Aluminosilicate | 24.0 | 24.0 | 24.0 |
| Sodium sulfate | 6.0 | 6.0 | 6.0 |
| Acrylic Acid/Maleic Acid Co-polymer | 4.0 | 4.0 | 4.0 |
| $C_{12-13}$ linear alkylbenzene sulfonate, Na | 8.0 | 8.0 | 8.0 |
| Sodium silicate | 3.0 | 3.0 | 3.0 |
| Carboxymethylcellulose | 1.0 | 1.0 | 1.0 |
| Brightener 47 | 0.3 | 0.3 | 0.3 |
| Silicone antifoam | 1.0 | 1.0 | 1.0 |
| DTPMPA[1] | 0.5 | 0.5 | 0.5 |
| Admixed |  |  |  |
| $C_{12-15}$ alkyl ethoxylate (EO = 7) | 2.0 | 2.0 | 2.0 |
| $C_{12-15}$ alkyl ethoxylate (EO = 3) | 2.0 | 2.0 | 2.0 |
| Perfume | 0.3 | 0.3 | 0.3 |
| Sodium carbonate | 13.0 | 13.0 | 13.0 |
| Sodium perborate | 18.0 | 18.0 | 18.0 |
| Sodium perborate | 4.0 | 4.0 | 4.0 |
| TAED[2] | 3.0 | 3.0 | 3.0 |
| Savinase protease (4.0 KNPU/g)[3] | 1.0 | 1.0 | 1.0 |
| Lipolase lipase (100.000 LU/1)[3] | 0.5 | 0.5 | 0.5 |
| Termamyl amylase (60 KNU/g)[3] | 0.3 | 0.3 | 0.3 |
| Sodium sulfate | 3.0 | 3.0 | 5.0 |
| Miscellaneous (water, etc.) | balance | balance | balance |
| Total | 100 | 100 | 100 |

[1]Diethylene Triamine Pentamethylenephosphoric Acid
[2]Tetra Acetyl Ethylene Diamine
[3]Purchased from Novo Nordisk A/S The resulting detergent compositions unexpectedly have improved chemical stability, flowability, and excellent dissolution characteristics.

Accordingly, having thus described the invention in detail, it will be obvious to those skilled in the art that various changes may be made without departing from the scope of the invention, and the invention is not to be considered limited to what is described in the specification.

What is claimed is:

1. A process for producing a composition comprising the steps of:

(a) providing a particulate material wherein said material comprises detersive surfactants selected from the group consisting of anionic surfactants, nonionic surfactants, cationic surfactants, zwitterionic surfactants, ampholytic surfactants, and mixtures thereof;

(b) subjecting at least a portion of said particulate material to plasma glow zone in which a gas is ionized to form free radicals on said portion of said particulate material, wherein said plasma glow zone is contained in a plasma chamber operated at a pressure of from about 1 mTorr to about 300 Torr and a power of from about 0.1 Watts to about 500 Watts;

(c) introducing a water-soluble, organic hydrophilic monomer into said chamber after said step (b) such that said organic hydrophilic monomer reacts with said free radicals on said portion of said particulate material so as to form a water-soluble coating on said portion of said particulate material.

2. The process of claim 1 wherein said organic monomer is selected from the group consisting of acrylates, methacrylates, acrylamides, methacrylamides, maleates, fumarates, vinyl ethers and mixtures thereof.

3. The process of claim 1 wherein said gas is selected from the group consisting of argon, helium, oxygen, nitrogen and mixtures thereof.

4. The process of claim 1 wherein said organic monomer is introduced in the form selected from the group of vapor, liquid or mixture thereof.

5. The process of claim 1 wherein said organic monomer is atomized in said chamber using acoustic nozzles.

6. The process of claim 1 wherein said gas is ionized using high frequency microwaves.

7. The process of claim 1 wherein said gas is ionized using high frequency radio waves.

8. The process of claim 1 wherein said gas is ionized using direct current electricity.

9. The process of claim 1 wherein said gas is ionized via pulsation.

10. The process of claim 1 wherein said detergent material is position outside of said plasma glow zone.

11. The process of claim 1 wherein said organic monomer is introduced outside of said plasma glow zone.

* * * * *